United States Patent
Pilcher et al.

(10) Patent No.: US 9,554,963 B2
(45) Date of Patent: *Jan. 31, 2017

(54) SYSTEM FOR TREATMENT OF SKIN CONDITIONS USING AT LEAST ONE NARROW BAND LIGHT SOURCE IN A SKIN BRUSH HAVING AN OSCILLATING BRUSHHEAD

(71) Applicant: L'Oréal SA, Paris (FR)

(72) Inventors: Kenneth A. Pilcher, Seattle, WA (US); Robert E. Akridge, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/157,783

(22) Filed: Jan. 17, 2014

(65) Prior Publication Data

US 2014/0135665 A1    May 15, 2014

Related U.S. Application Data

(63) Continuation of application No. 11/969,447, filed on Jan. 4, 2008, now Pat. No. 8,641,702.

(51) Int. Cl.
*A61H 7/00* (2006.01)
*A46B 15/00* (2006.01)
*A61N 5/06* (2006.01)
*A46B 13/02* (2006.01)
*A61B 18/00* (2006.01)

(52) U.S. Cl.
CPC .......... *A61H 7/005* (2013.01); *A46B 15/0002* (2013.01); *A46B 15/0034* (2013.01); *A61N 5/0616* (2013.01); *A46B 13/02* (2013.01); *A46B 2200/102* (2013.01); *A61B 2018/00898* (2013.01); *A61B 2090/065* (2016.02); *A61H 2201/0153* (2013.01); *A61H 2201/0176* (2013.01); *A61H 2201/10* (2013.01); *A61H 2201/1215* (2013.01); *A61H 2201/165* (2013.01); *A61H 2201/1678* (2013.01); *A61H 2205/022* (2013.01); *A61N 2005/063* (2013.01); *A61N 2005/0626* (2013.01); *A61N 2005/0644* (2013.01); *A61N 2005/0645* (2013.01); *A61N 2005/0652* (2013.01); *A61N 2005/0653* (2013.01); *A61N 2005/0663* (2013.01); *A61N 2005/0666* (2013.01)

(58) Field of Classification Search
CPC ................... A61B 2018/00452; A61B 18/203
USPC ................................. 606/9, 131; 607/88–90
See application file for complete search history.

(56) References Cited

U.S. PATENT DOCUMENTS

| | | |
|---|---|---|
| 2004/0147984 A1 | 7/2004 | Altshuler et al. |
| 2004/0260210 A1 | 12/2004 | Ella et al. |
| 2005/0251242 A1 | 11/2005 | Bousfield et al. |

(Continued)

*Primary Examiner* — William Thomson
*Assistant Examiner* — Dacheng Xie

(57) ABSTRACT

An apparatus and corresponding method for treatment of skin conditions which includes a brushhead member which comprises a first portion which includes a plurality of rings of bristle tufts, the first portion oscillating in operation through a selected angle at a selected frequency and a second portion which also includes a plurality of rings of bristle tufts concentric with the first portion, the second portion remaining stationary in operation. At least one monochromatic light source is included, providing light directed from the brushhead in a direction substantially the same as the bristle tufts, such that the light impinges on the area of skin of the user acted on by the oscillating brushhead.

12 Claims, 15 Drawing Sheets

(56) References Cited

U.S. PATENT DOCUMENTS

| | | |
|---|---|---|
| 2005/0277950 A1 | 12/2005 | Pilcher et al. |
| 2005/0278876 A1 | 12/2005 | Roth et al. |
| 2007/0123808 A1* | 5/2007 | Rhoades .............. A45D 24/007 601/73 |
| 2008/0131834 A1 | 6/2008 | Shepherd et al. |
| 2008/0172112 A1 | 7/2008 | Gourgouliatos et al. |

* cited by examiner

SYSTEM FOR TREATMENT OF SKIN CONDITIONS USING AT LEAST ONE NARROW BAND LIGHT SOURCE IN A SKIN BRUSH HAVING AN OSCILLATING BRUSHHEAD

TECHNICAL FIELD

This invention relates generally to the treatment of skin conditions in humans, and more specifically concerns the treatment of skin conditions using a narrow band light source in a skin brush with an oscillating brushhead.

BACKGROUND OF THE INVENTION

There are many well-known bacteria which cause various medical conditions. The bacteria *P. acnes* has been indicated to be responsible for the acne skin condition in humans, generally known as acne vulgaris, which is the most commonly treated skin condition in the United States. Acne has long been problematic for young adults, but older adults are often affected as well. Effective acne treatment is emphasized, particularly for young people, because of the often long-term consequences, both physical and emotional, which occur due to the unsightly acne skin condition.

Because acne primarily occurs during adolescence, when self-image is being formed, even a mild case can have a profoundly negative effect on the psychosocial development of the individual, including school performance. Further, a moderate to severe acne condition, with its usual long-term scarring effects, can cause disfigurement, often significant, that persists throughout life, which can affect career choice and employment opportunities.

While, as indicated above, acne occurs most frequently in young (adolescent) adults, it is not always resolved by the end of the teenage years and may persist into the 40's for certain individuals. In some cases, the onset of acne may not occur until the mid-20's.

For all the above reasons, it is important to recognize that acne is a significant medical condition, and that it affects a significant part of the population, and many age groups.

Acne treatment includes diet restrictions, antibiotics (both oral and topical), as well as exposure to sunlight and other light sources. Retinoids and hormonal manipulation treatment are also used. Diet restrictions are typically problematic, with unpredictable results. Oral antibiotics have been successfully used to treatment acne, but can have disadvantages, including yeast vaginitis, gastrointestinal side effects and photosensitivity. Retinoids are not advised for women of child-bearing potential and often cause xerosis (dry skin), erythema, cheilitis, conjunctival irritation and alopecia, while hormonal therapy expose the patient to risk of thromboembolism, feminization (in men) and other undesirable effects. Topical antibiotic applications are also used for acne treatment, including retinoids, benzoyl peroxide, salicylic acid and antibiotics. Each of these has their specific undesirable side effects, including undesirable skin surface reactions in some cases.

Light therapy has also been used for acne treatment, including exposure to sunlight. While ultraviolet light has been used in the past in clinical situations to treat acne, such treatment is no longer recommended because of the risk of skin cancer. Existing clinical devices using ultraviolet light are expensive and sufficiently risky that they must be used by medical professionals. The effect of light treatments has in some cases been enhanced by the use of selected photosensitive chemicals. However, such therapy, using a combination of light and selected chemicals, is often uncomfortable, causing stinging, erythema, epidermal exfoliation and hypersensitivity.

New developments in acne treatment involve narrow band light. These developments are illustrated in the following patents and patent applications: U.S. Pat. No. 5,549,660 to Mendes et al uses a light source with a wavelength of 660 nanometers. This, however, has not proven to be particularly effective. Patent Applications No. 20010028227 and 20010023363 to Lys and Harth teach, respectively, the use of light-emitting diodes (LEDs) and 400 watt metal halide lamps which are filtered to emit light in the 407-420 nanometer wavelength range, which has been shown to be effective against certain acne bacteria. The lamps are used to illuminate the entire face. They are large and expensive. LEDs on the other hand are small (on the order of 0.100") and relatively low cost.

Further, metal halide lamps are inefficient relative to power required and create significant problems in the skin area being treated. A clinical setting and supervision are required. In contrast, LEDs have efficiencies of 15-20%.

There is no effective home use treatment for acne using light. It is hence desirable that an effective treatment of acne using light be developed which is safe, inexpensive and simple to use at home.

SUMMARY OF THE INVENTION

Accordingly, the present invention includes an apparatus for treatment of skin conditions, comprising: a housing member for the apparatus; a brushhead member adapted to fit to the housing member comprising a first portion which includes a plurality of rings of bristle tufts, the first portion oscillating in operation through a selected angle; a driving assembly for the brushhead member; and at least one source of light having a wavelength suitable for treatment of a selected skin condition, wherein said light is directed from the brushhead member.

The present invention further includes a method for treatment of skin conditions, comprising the steps of: applying a back and forth stress action to the skin by a skin brush appliance which rotates through a selected angle at a selected frequency to stretch the skin in opposing directions without damaging the skin; and applying light to the area acted on by the skin brush from a brushhead portion of the skin brush, the light having at least one wavelength which is suitable for treatment of a selected skin condition.

BEST MODE FOR CARRYING OUT THE INVENTION

As indicated above, both natural sunlight and light from particular sources, including a metal halide lamp with a filter to provide light with a selected wavelength have been used to treat acne vulgaris (hereafter referred to as acne). Filtered light sources are also used to diagnose acne. For some time, the reasons for the success of sunlight were not clearly understood. Further, sunlight treatment was and is accompanied by the undesirable effects of burning and even skin deterioration and cancer, caused by the ultraviolet (UV) wavelengths in sunlight.

Acne is a rather complicated skin condition, which involves basically three skin processes or stages. The first process or stage in the development of acne is formation of a microcomedone (plug), which is a microscopic concentration of keratinocytes, sebum and colonies of bacteria formed in the follicular infundibulum (skin pore). The microcomedone then increases in size, with increased adherence of cornified cells, resulting in closure of the infundibulum (pore), which in turn promotes a microaerobic environment.

The second process/stage is known as seborrhea, involving an increased rate of sebum production, which supplies nutrients for the *P. acnes* bacteria. This occurs within a pilo-sebaceous unit area confined by the closed comedone resulting from the first process.

In the third process, microbial colonization occurs in the resulting sebum-rich environment. When the infundibulum becomes blocked by the microcomedone, the balance within the pilo sebaceous unit is upset; if the conditions of pH and oxygen are correct within the closed comedone, the bacteria grows in number and produces a pathogenic effect, resulting ultimately in an acne lesion (pimple). This process can include damage to the follicular walls and extrusion of lipids.

It has been discovered that the *P. acnes* bacteria include certain porphyrins, which, upon absorbing light in the visible spectrum, in the presence of oxygen, results in the exciting of an electron in its structure. The excited electron then breaks an adjacent oxygen molecule into singlet oxygen free radicals. The reactive oxygen initiates a series of chemical reactions, which ends in the killing of the bacteria.

As discussed briefly above, previous light sources used in the treatment of acne have suffered from a number of undesirable side effects. Specifically, these include the presence of secondary wavelengths in the emitted light, relatively poor efficiency, in terms of input power requirements of broadband light sources, the expense and complexity of filtering broadband light when only a narrow band is actually to be used, significant heat generation by the light devices, requiring specialized, expensive equipment and complicated optic systems in order to limit the exposure of the skin. Exposure time is excessive for practical home use. All of the previous light treatment devices have required the supervision of a medical professional.

Figure 1:
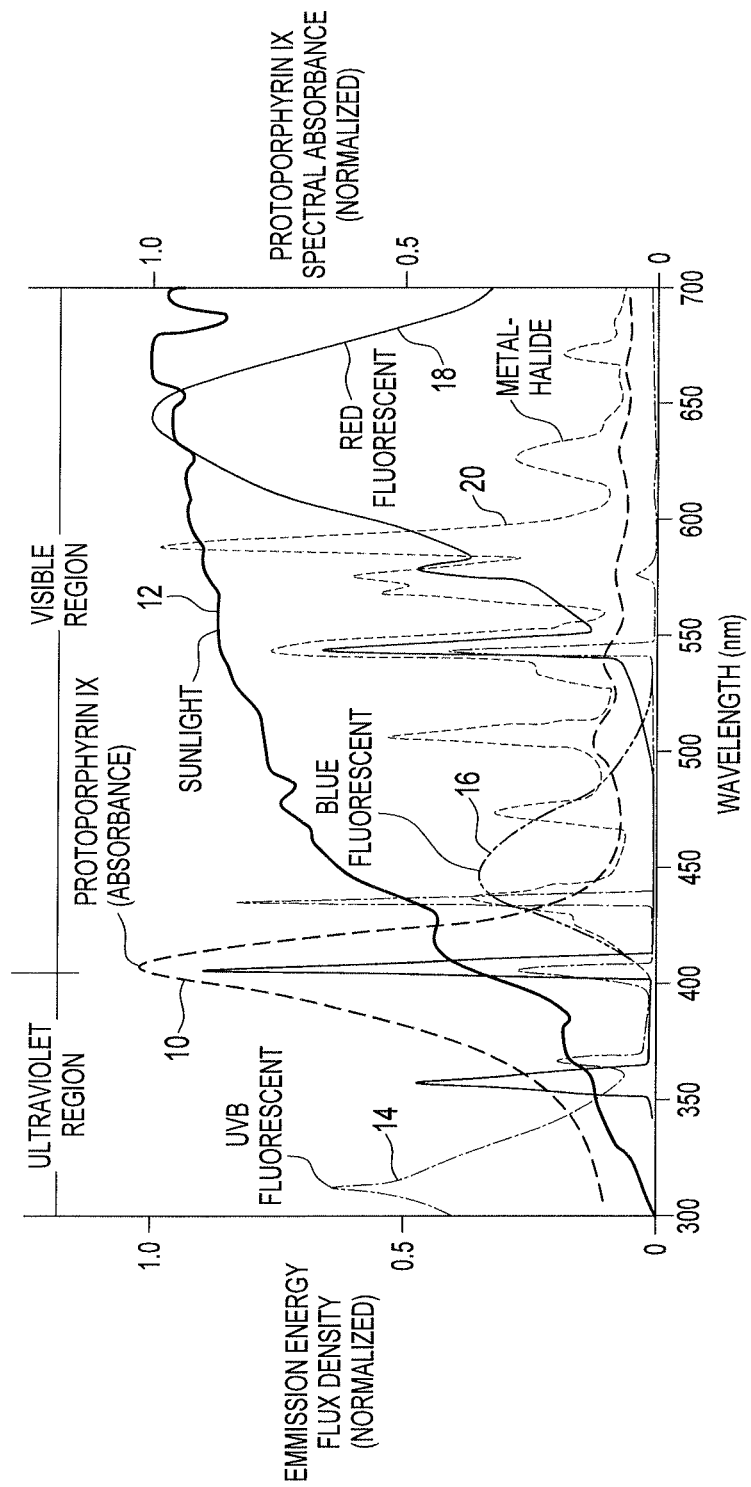
FIG. 1 is a diagram showing the emission spectra of sunlight and other traditional phototherapy light sources relative to the absorption spectrum of *P. acnes* porphyrins.

In the present invention, a light source is used which actually produces, without filtering, narrow band light which closely approximates that of the primary visible light absorption characteristic of the porphyrins in *P. acnes* bacteria, i.e. an absorbance spectra peak of 409 nanometers (violet). The light produced by the apparatus of the present invention stimulates the *P. acnes* porphyrins with light at that wavelength. FIG. 1 illustrates generally the peak absorbance of the porphyrins and the spectra of various light sources. The absorbance peak of *P. acnes* porphyrins at 409 nanometers is referred to at 10, while sunlight emission spectrum is referred to at 12. Individual ultraviolet, blue fluorescent and red fluorescent light sources are referred to at 14, 16 and 18, respectively, while the spectrum of a metal halide source is referred to at 20. Sunlight radiation, particularly in the ultraviolet bands, is associated with skin deterioration and cancer, while the red and blue fluorescent bulbs and metal halide lights have relatively little wavelength content at the key wavelength of *P. acnes* porphyrins, making them highly inefficient for treatment of acne.

Figure 2:
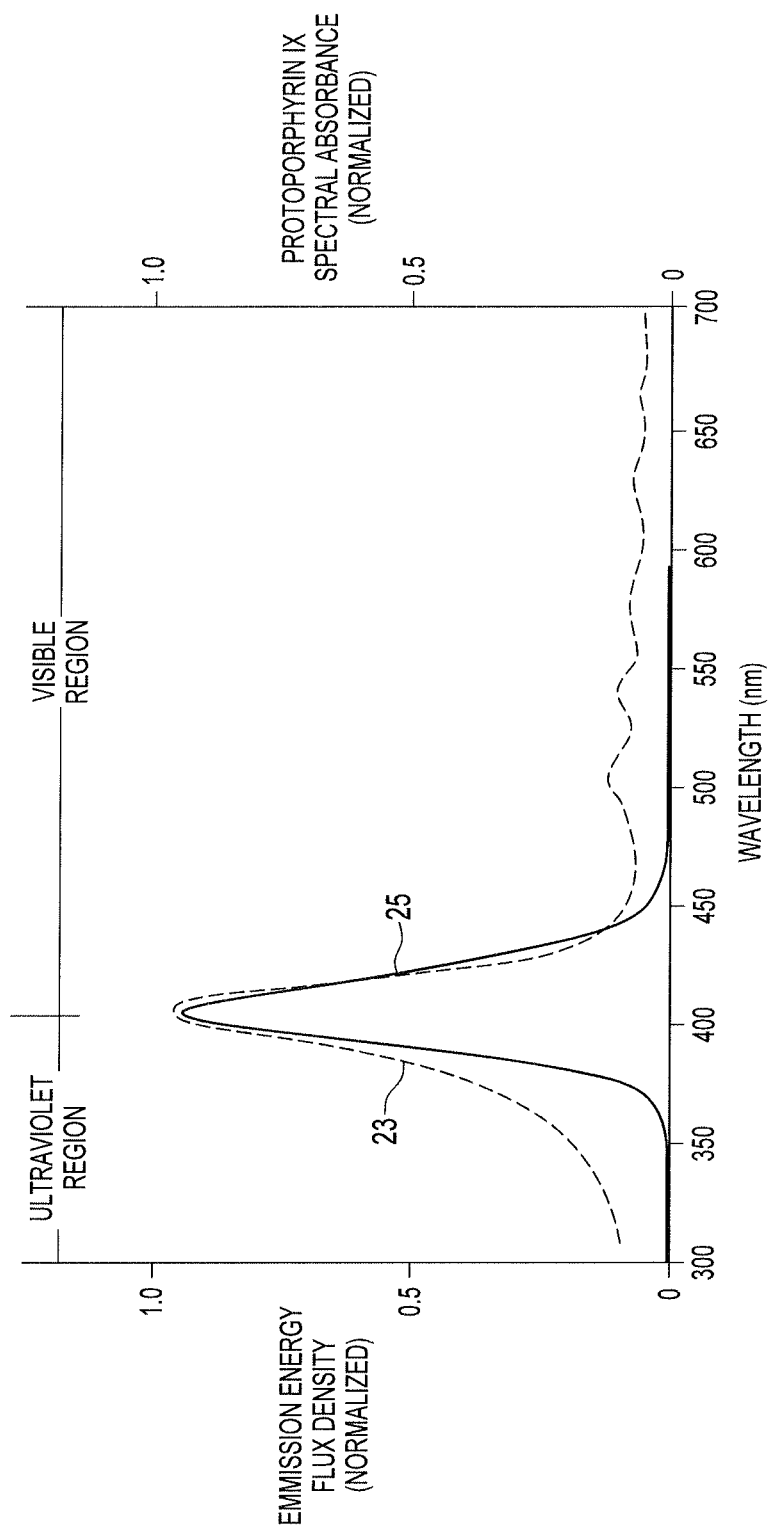
FIG. 2 is a diagram showing in more detail a portion of the diagram of FIG. 1, comparing the emission spectrum of a violet blue LED (405 nanometers wavelength) with the absorbance spectrum of *P. acnes* porphyrin.

The present invention includes a light source, which emits light in a narrow band which closely approximates the peak absorbance wavelength of the *P. acnes* porphyrins, 405 nanometers. FIG. 2 shows the absorbance spectra 23 of a typical *P. acnes* porphyrin relative to the emission spectra 25 of the light source used in the invention. The light source is unfiltered, so there is no loss of light energy. The present invention is configured and adapted for convenient, economical and safe home use, without the aid of a medical professional.

Figure 3A:
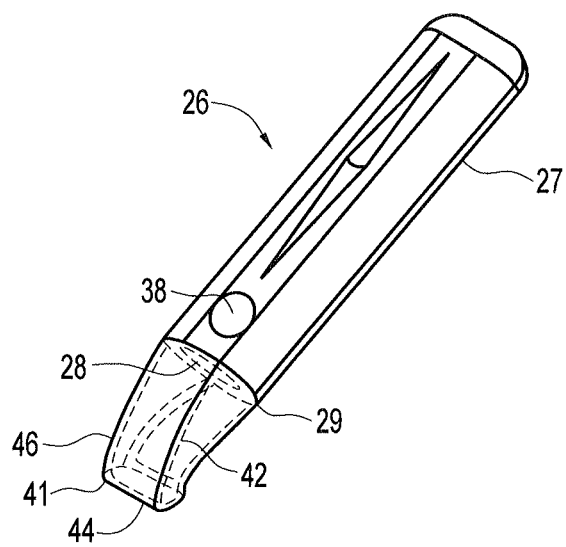
FIGS. 3A, 3B and 3C show a hand-held device of the present invention for treatment of acne.
Figure 3B:
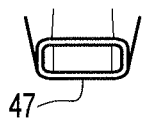
Figure 3C:
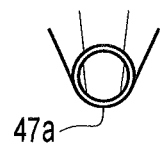

The first embodiment of the invention is shown in FIG. 3. It is a hand-held apparatus appropriate for short-term light exposure, suitable for home use. The apparatus, referred to generally at 26, includes a handle 27 and a monochromatic light source 28, which is mounted at the forward end 29 of the handle and emits radiation at the desired wavelength of 405 nanometers. In the embodiment shown, the monochromatic light source is a solid-state light source, in particular an LED or LED array or laser diode. Alternatively, the light source could be an organic LED or electroluminescent element or other monochromatic light source. More specifically in the embodiment shown, light source 28 is a 4×4 array of 405 nanometer LEDs, which is mounted on a common interconnecting substrate. Other size arrays could, however, be used. The array provides greater intensity and/or increased coverage relative to a single LED. Handle 27 in the embodiment shown is generally rectangular, sized and configured for convenient hand-held use, curved at the corners and along the longitudinal edges for convenience of the user. The LED array is driven by a constant current circuit powered by a battery producing approximately 15-30 mA and preferably 20 mA current for each LED. The constant current circuit and battery are both located in the handle. Much higher current arrangements could be used, up to 750 mA and even greater.

Each LED in the array emits relatively intense light, designed for site-specific treatment of a single acne lesion or for moving across the skin in the treatment of a larger area. The intensity of the emitted light is approximately 20 milliwatts per square centimeter or less, which is effective but significantly less than sunlight. This could be greater, up to 500 mw/cm$^2$. Presently, LEds are available in 200-250 mw/cm$^2$, at 350-700 mA. This will likely change with further LED development. The emitted light is approximately 40 times more efficient in stimulating the *p. acnes* porphyrins than sunlight. The exposure time using the apparatus of FIG. 3 will typically be a matter of a few minutes, once or twice a day. A conventional battery is typically used in the apparatus, preferably rechargeable. The device is activated by an on/off button 38.

Extending from the forward end 29 of handle 27 is an optical light directing pipe or "scrambler" 42, which conducts the emitted light from the LED light source 28 to the surface of the skin being treated. The light conductor 42 is a transparent body which can be made from acrylic and coated internally with a white plastic which includes titanium dioxide so that light reflects and refracts and is radiated back into the interior of the conductor, exiting at the outlet port 44 thereof onto the skin of the user.

The apparatus 26 may also include optical devices such as lenses (not shown), which will further focus the emitted light onto a desired spot size.

Extending closely around the light conductor 42 is an optional removable light spreader 46. It terminates in a free end 47, which is in approximately the same plane as the conductor 42. The end of spreader 46 through which the emitted light comes can have various configurations, including rectangular (47), circular (47a), elliptical or other configurations, depending upon the desired configuration of the radiation.

Handle 27 can also house additional electronic controls for the device. These can include a circuit for temporary disabling of the apparatus if it is not in a correct position for safe use, such as in contact with a surface; a timing element which controls the operation of the device to ensure that the exposure time is correct, an audible or visual indicator for indicating to the user when the desired exposure time has expired, and an indicator element which indicates battery charge status.

The device 26 of FIG. 3 is advantageous because of the use of the monochromatic LEDs, which have the advantage of low heat generation and efficient production of only the desired light wavelength. The device 26 is thus a convenient, hand-held device, which is conveniently usable at home by non-medical personnel.

Figure 4A:
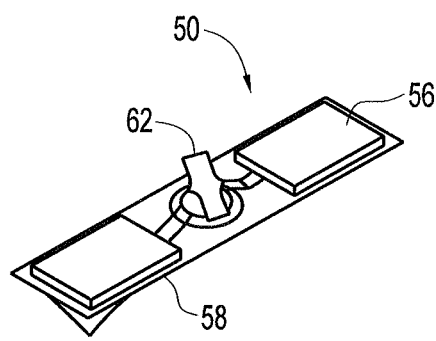
FIGS. 4A, 4B, 5 and 6 show other embodiments using light to treat acne embodying the principles of the present invention.
Figure 4B:
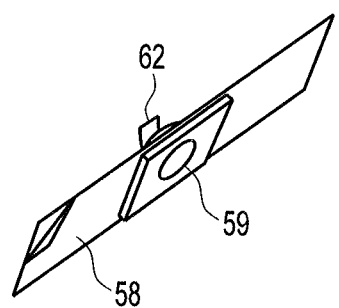

FIGS. 4A and 4B show an embodiment, which is attachable directly to the skin, and designed to be used for longer periods of time than would be convenient or comfortable for the hand-held device of FIG. 3. The device 50 is designed for spot treatment of an area, i.e. one to five centimeters across. The light source (not shown specifically) is integral to the device and comprises a single 405 nanometer LED driven by a control circuit on a common interconnecting substrate with batteries 56, all mounted on an adhesive plastic strip 58. The adhesive plastic strip 58 is designed to be attached to the skin for the length of the treatment. Other attachment means besides adhesive, however, can be used. These could include Velcro® strips, or a mask or headband element of some kind. The LED emits relatively low intensity light, less than 5 milliwatts per centimeter, through a light outlet port 59.

The apparatus 50 includes a convex lens (not shown), which encapsulates the LED and produces a small air gap, on the order of 2-5 millimeters, between the light source and the skin. This spreads the light and directs it through port 59 to a small spot on the skin, desirably one centimeter or so in diameter. A switch element 62 is provided which can be conveniently turned by the user to turn the LED on and off. When the switch is in the on position, the LED is activated and the light is provided directly onto the acne lesion until the battery is discharged.

Alternatively, the battery and the drive circuit could be positioned in a module, which is separate from the unit 50, with wires connecting the drive circuit and battery to the LED on the unit. Additional electronics could be provided for indicating expiration of exposure times and/or battery charge status or other information. The device/unit of FIGS. 4A and 4B is designed for longer-term exposure (a few hours) of a small area at low intensity. The attachment member results in the treatment being "hands free".

Figure 5:
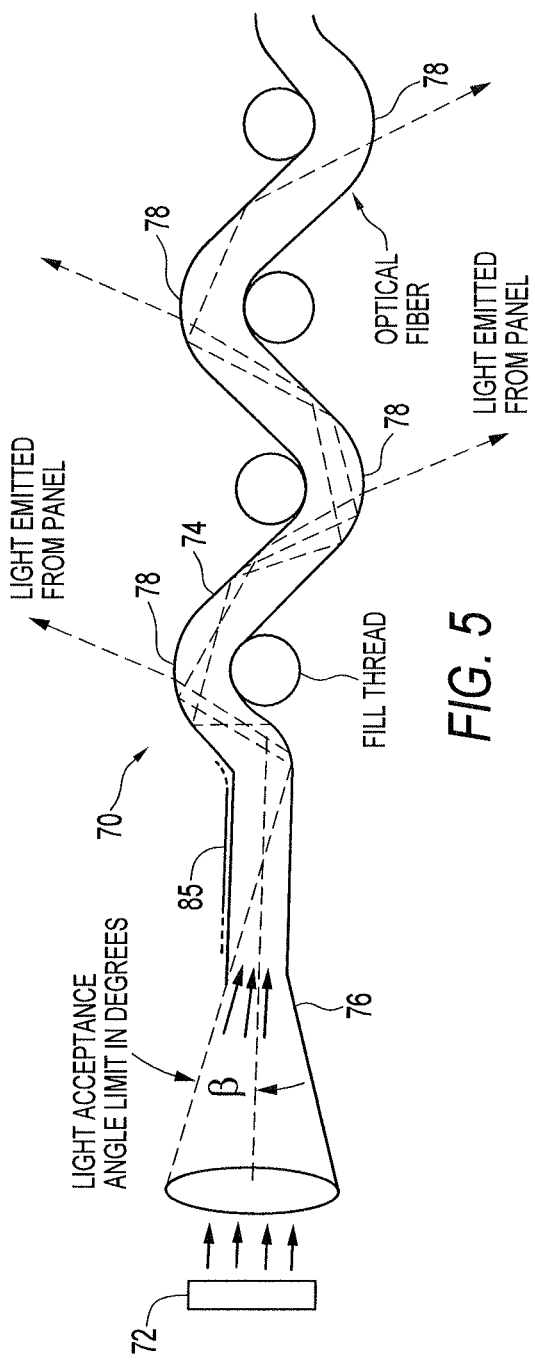

Another embodiment for attachment to the skin of a user over a large treatment area (greater than 100 cm$^2$) is shown in FIG. 5. A device 70 produces a pattern of light emission at relatively low intensity (less than 5 milliwatts per centimeter squared), although this value could be higher. The exposure time for the treatment area will be on the order of a few hours. Device 70 includes a monochromatic light source 72 and a woven fabric patch 74 of optical fiber. The fabric is sufficiently flexible that the entire patch will conform to the shape of the skin treatment area. The patch may also be preformed to match the contour of a particular part of the face or body.

The light from LED 72 is applied to the fiber bundle 76 of the patch over a specified acceptance angle. Light escapes from the fiber patch at the bends 78 in the weave, as shown in FIG. 5, which results in a relatively uniform distribution of light over the surface of the fabric. A reflective element or layer 85 redirects any light escaping from the upper side of the patch back toward the skin. The light source, battery and drive circuit can be mounted on the fabric patch, but alternatively can be mounted on a module, which is coupled to the fabric. The fabric patch can be attached to the skin for "hands-free" treatment by various means including adhesives, etc.

Figure 6:
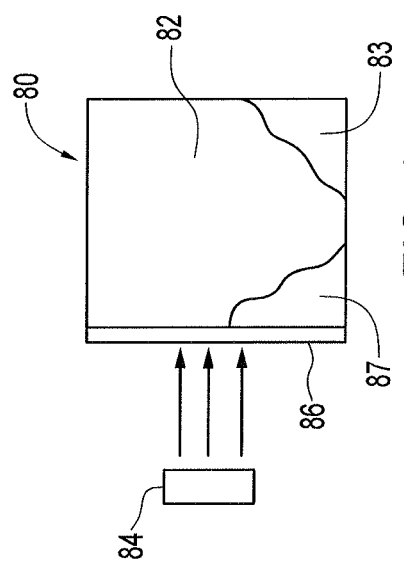

FIG. 6 shows another "patch" embodiment designed for attachment to the skin for treatment of a relatively large area, with low intensity (less than 5 mW/cm$^2$). Patch 80 includes a molded plastic sheet 82 and a lower adhesive layer 83, which secures the device to the skin temporarily and is transmissive for the emitted light. The sheet 82 is activated by a light source 84 at an edge 86 thereof. The patch 80 is sufficiently flexible to conform to the shape of the treatment area. Additionally, the patch may be preformed to match the contour of a particular part of the face or body.

The lower surface of sheet 82 proximal to the skin is molded such that it has a shallow arrangement of impressions, which cause the light within the sheet from the monochromatic light source to be emitted perpendicular to its surface and toward the skin. The pattern of the impressions is such that the output of light is relatively constant over the entire surface area of the sheet. A reflective element 87 overlaying sheet 82 redirects any light escaping from the upper side of the patch back toward the skin.

The devices of FIGS. 4A, 4B, 5 and 6 are all low intensity, longer-term (a few hours) treatment devices. They are all secured or attached to the skin in some way, either by adhesives, a strap or other means, so that the devices can be used essentially hands-free for the recommended treatment time.

Hence, the present invention is directed toward an efficient, safe treatment for acne using light, in which a monochromatic source of light having a specific wavelength is used, which is substantially coincident with the peak absorbance of the porphyrins present in the *p. acnes* bacteria. The light is produced by an LED or other inherently monochromatic light source, such as lasers, for instance, and positioned in either a hand-held device or patch-like devices and controlled so that the devices are convenient, safe and reliable to be used by a non-medical professional at home.

Figure 7:
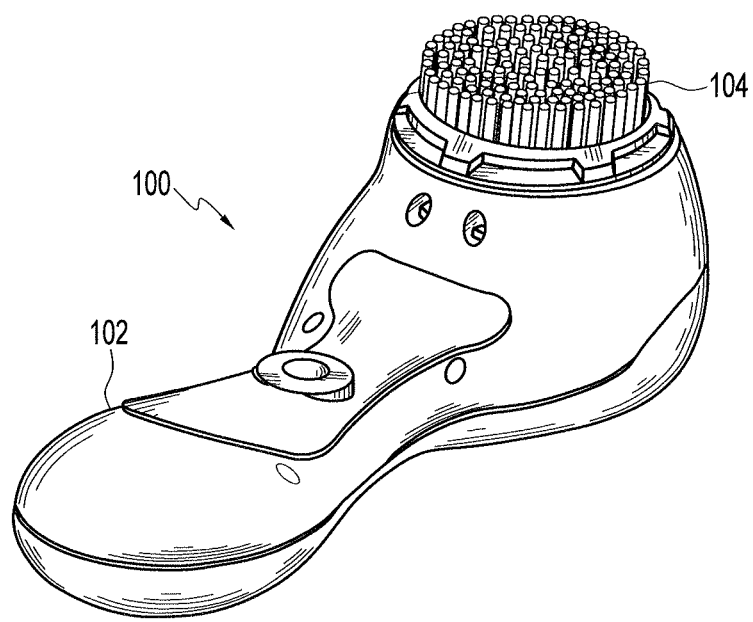
FIG. 7 is a perspective view of a skin brush with an oscillating brushhead.

FIGS. 7-25 show additional embodiments which incorporate narrow band light sources, such as LEDs or lasers or other similar devices, for treatment of specific skin conditions, including acne as well as other skin conditions, in an oscillating brushhead portion of a power skin brush. A representative skin brush appliance is shown generally at 100 in FIG. 7. The appliance includes a handle portion 102 and a removable brushhead portion 104. Such a skin brush is shown and described in co-pending patent applications Ser. Nos. 10/873,584 and 10/873,352, both of which are owned by the assignee of the present invention. The contents of both of those applications are hereby incorporated by reference.

Figure 8:
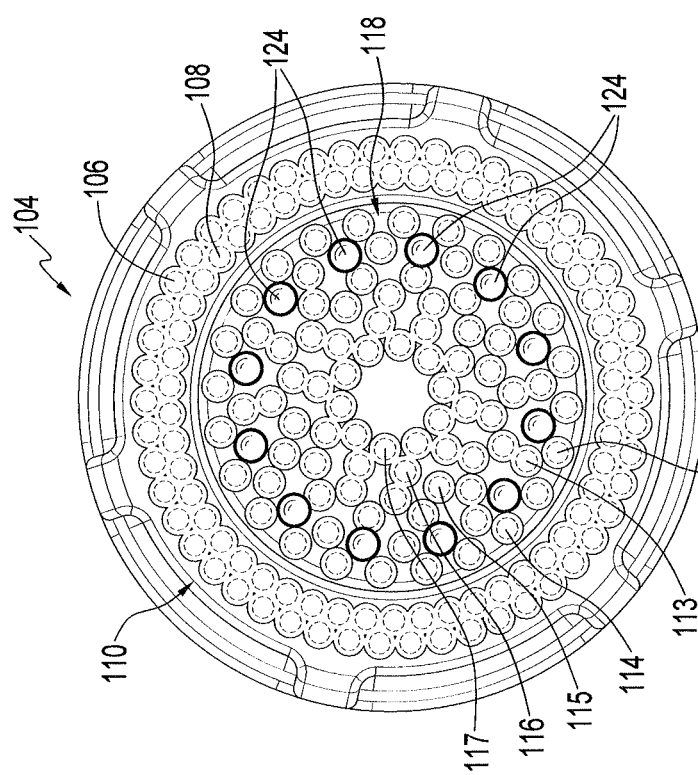

In the embodiments shown in FIGS. 8-25, the brushheads of the appliance 100 have a particular configuration. However, it should be understood that other brushhead configurations and arrangements can be used in combination with the illustrated light sources. The brushhead arrangement (FIG. 8 is exemplary) includes two concentric outer rings of bristle tufts 106 and 108 in an outer portion 110 and 6 concentric inner rings 112-117 of bristle tufts in an inner portion 118. The rings 106 and 108 in outer portion 110 remain stationary in operation, while rings 112-117 in inner portion 118 rotate through a selected angle. Generally, this angle is in the range of 2-30°, with a preferred range of approximately 5-20°. The oscillation occurs within a sonic frequency range of 60-200 Hz and preferably is approximately 176 Hz. The outer portion 110 comprising outer rings 106 and 108 provides a splash barrier for the oscillating rings of the inner portion 118, as well as a stationary contact ring by which the oscillating action of the bristle tufts of the inner portion creates localized shear skin stresses for effective cleansing of the skin without damage or harm to the skin. This action is described in more detail in U.S. patent application Ser. No. 10/345,909, which is owned by the assignee of the present invention, the contents of which are hereby incorporated by reference.

In the embodiment shown, there are 50 tufts in each outer ring 106 and 108, while inner rings 112 and 113 have 24 tufts, rings 114 and 115 have 15 tufts, and rings 116 and 117 have 10 tufts each. It should be understood, however, that this specific arrangement can be varied. In another embodiment, the two outer rings have 40 tufts each, while the six inner rings have 24, 24, 14, 14, 10 and 10 tufts, respectively. The separation between the inner set of rings and the outer set of rings is 0.154 inches center-to-center, while the edge-to-edge distance between tufts is 0.084 inches at the base of the tufts. The tufts are 0.070 inches in diameter. Each tuft comprises a number of individual bristles, typically approximately 270, with each bristle having particular dimensions, described in more detail in the '584 application. Another embodiment has 164 bristles per tuft. The bristle diameter in one example is 0.004 inches, with a length in the range of 0.250-0.600 inches, and a preferred range of 0.300-0.450 inches. Alternatively, the brushhead could comprise a basic plurality of bristle tufts, with the brushhead moving back and forth about a rest or neutral position. The movement could be longitudinal, lateral, or other more complex motions, as long as the movement creates localized shear stress for cleansing of the skin.

Arranged in the brushhead 104 are a plurality of individual light sources, so that light of selected wavelength(s) emanates from the brushhead, although in some embodiments, a single light source can be used.

The individual light sources are typically narrow band, such as for example, approximately 405 nanometers (deep blue), used specifically to treat acne, as described above. Other examples include specific wavelengths to treat psoriasis, skin rejuvenation, fungal infections, bacterial infections, collagen renewal, as well as certain skin cancers. These will typically each require their own specific wavelengths, which are either presently known or will become known. In certain cases, broad band light sources may be used to treat particular skin conditions. Other specific wavelengths include 210 nm (UV-C), 470 nm (blue), 547 nm (green) and 627 nm (red). The power output of these light sources can vary. Presently, as indicated above, LEDs are available in 200-250 mw/cm$^2$ at 350-700 mA. The LEDs could be continuous light or pulsed. In general, for pulsed light, the frequency could be 0.1 Hz-10 KHz, with a flash duration of 1 μs-5 ms and a "dark" period of 0.0001-10 seconds. Preferred ranges of frequency and the light/dark duty cycle will vary depending on the particular application.

Figure 21:
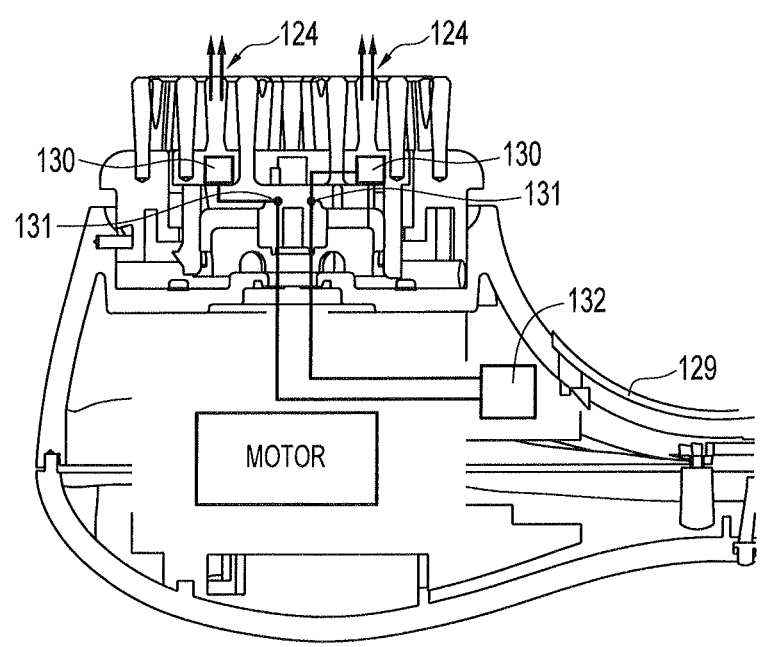
Figure 22:
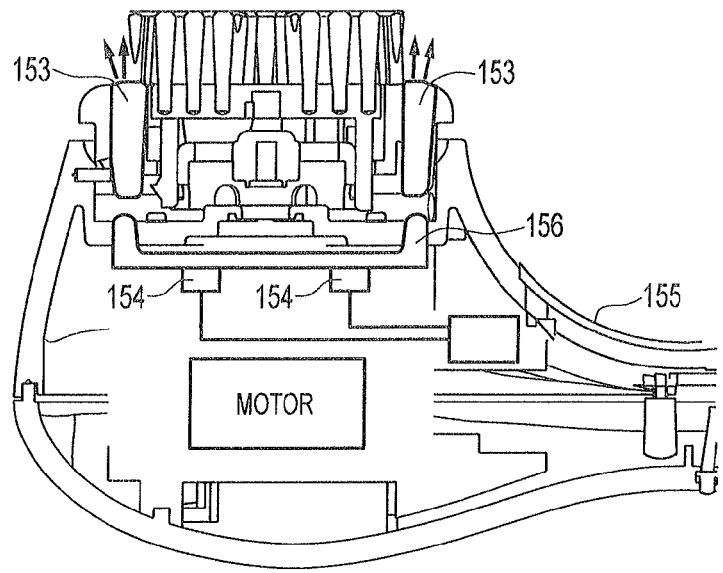

FIG. 8 shows one example of a brushhead/light source combination, using the particular brushhead described in detail above. A plurality of individual light sources 124-124 are positioned within the inner (oscillating) portion of the brushhead. In this example, also referring to FIG. 20, narrow band light emitters 126-126 are located in the handle 129 of the appliance, along with a driver circuit 127. The light is directed through individual transparent bristle tufts in the brushhead which act as light sources/transmitters 124. In the embodiment of FIG. 8, there are a total of 12 bristle tufts which transmit light from the brushhead, equally spaced around the brushhead. However, a different number of light transmitters can be used, with different spacing. In the embodiment of FIG. 8, all of the emitters 126-126 have the same wavelength. FIG. 21 is also applicable relative to an arrangement where the light sources/transmitters in the brushhead are transparent bristle tufts 124. In FIG. 21, however, light emitters 130 are also positioned in the brushhead, with electrical connections 131 connecting the emitters 130 to the driving circuit 132 in the handle 129 of the appliance.

Figure 9:
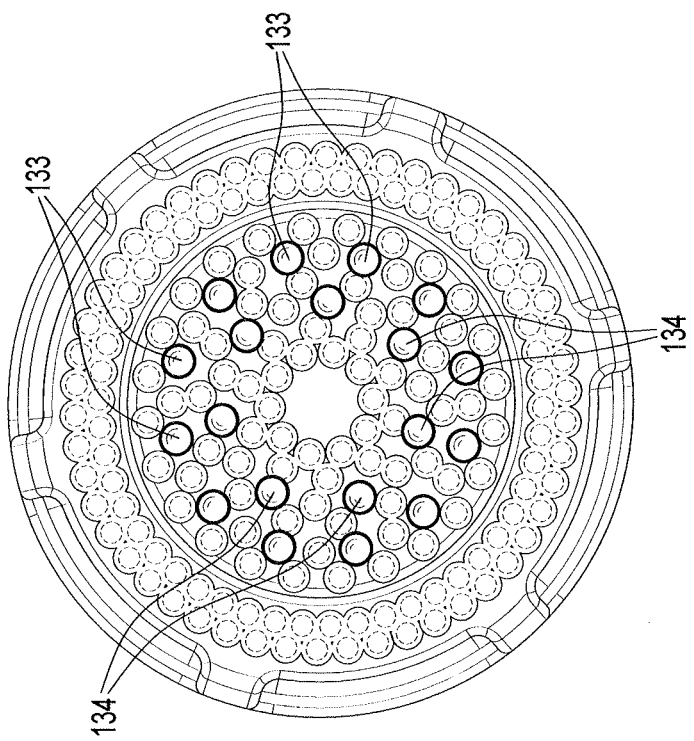
FIGS. 8-19 show top views of oscillating brushheads incorporating various arrangements of narrow band light sources.

FIG. 9 shows a variation of FIG. 8 in which two sets of spaced light-transmitting bristle tufts are used. One set 133 is a ring of spaced bristle tufts through which a first narrow band wavelength is transmitted, while a second set 134 is a ring of spaced bristle tufts through which a second narrow band light wavelength is transmitted. Hence, the present combination can include a single wavelength or multiple (different) wavelengths, including more than two if so desired. Alternatively, the two sets of light wavelengths could be broadband, each covering a selected range of wavelength, or a combination of narrow and broadband sources, depending on the particular application.

Figure 11:
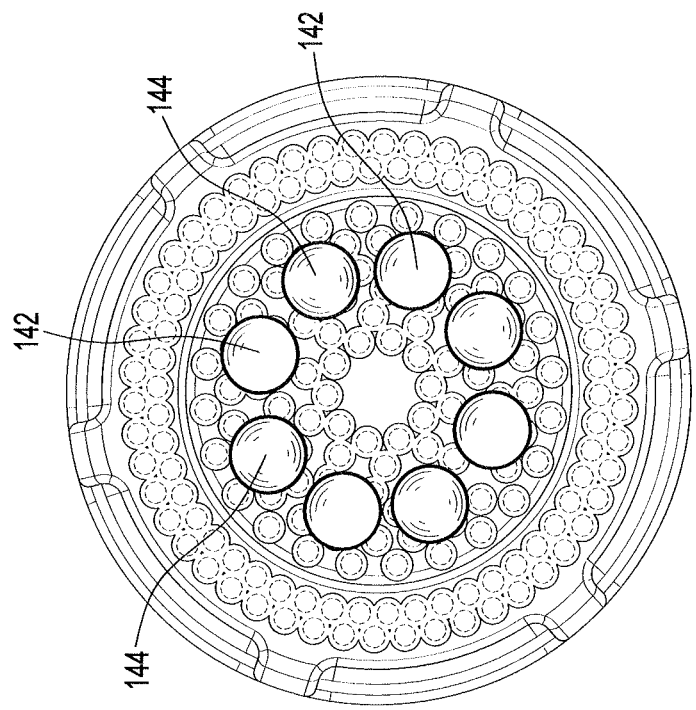
Figure 10:
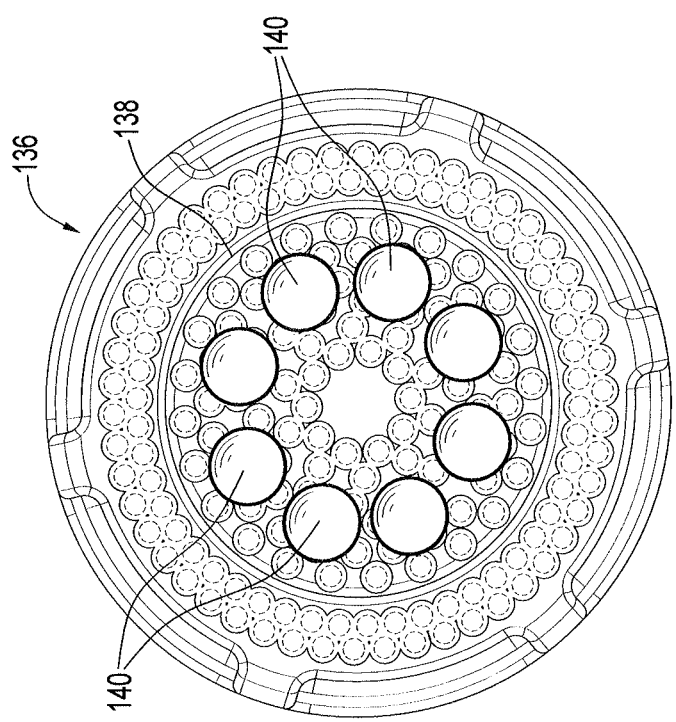

Alternatives to FIGS. 8 and 9 are shown in FIGS. 10 and 11. FIG. 10 shows a brushhead 136, as described above. Embedded in the inner, oscillating portion 138 of the brushhead are a plurality of self-contained light emitters 140-140, separate from the bristle tufts themselves. The light emitters 140 are equally spaced around oscillating portion 138, although they could be positioned in a different arrangement. The driver(s) for the light emitters are located in the handle of the appliance. FIG. 11 shows a variation of FIG. 10, in which the light emitters have more than one wavelength. For instance, light emitters 142-142 could be one selected wavelength, while light emitters 144-144 (alternating with emitters 142) could be another selected wavelength. Additional light emitters, with additional wavelengths, can also be used. Also, the emitters can be broadband, covering a selected range of wavelength or a combination of narrow and broad band wavelengths. The wavelengths of the light sources will be associated with particular skin treatments.

Figure 13:
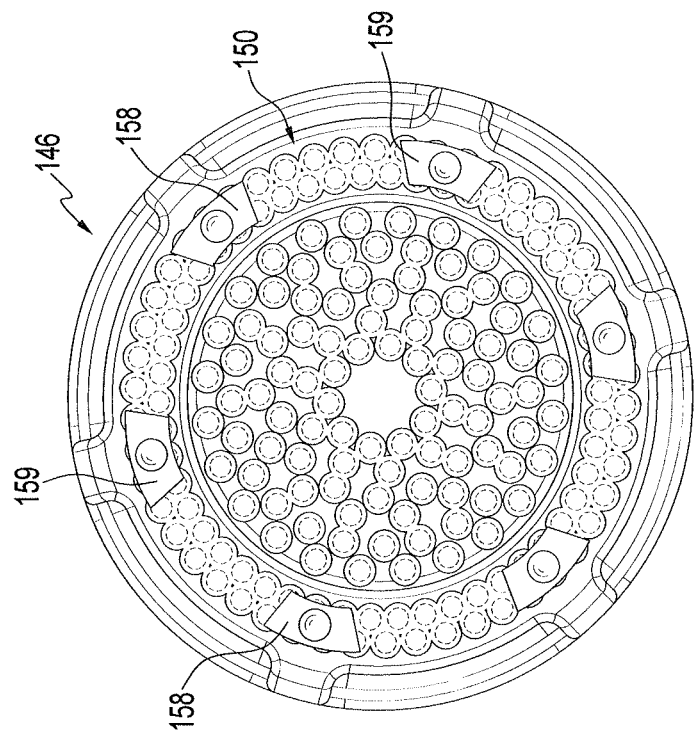
Figure 12:
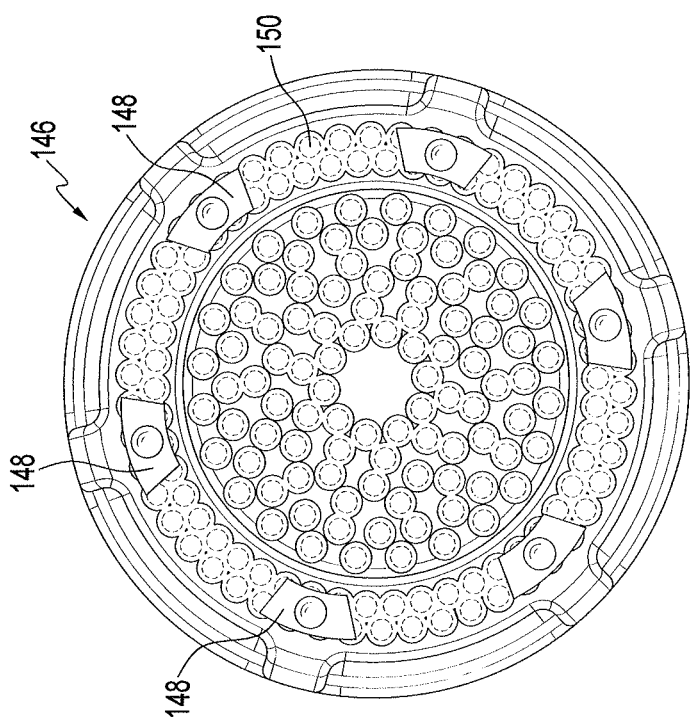

FIGS. 12 and 13 show other embodiments, with FIG. 12 including a plurality of single, narrow band light sources/transmitters 148-148 in the outer (stationary) portion 150 of brushhead 146. In this embodiment, also referring to FIG. 22, individual light pipes 153-153 are used as light sources/transmitters, positioned in slots in the brushhead, with light emitters 154-154 positioned in the handle 155, the light from emitters 154 being transmitted to the light pipes directly or through an intermediate light pipe 156 positioned in the handle 155.

FIG. 13 shows a variation of the arrangement of FIG. 12, in which individual light pipes in slots in outer portion 150 of the brushhead 146 transmit light of more than one wavelength, using different wavelength emitters. In this case, light from light pipes 158-158 is one wavelength while light from light pipes 159-159 (alternating with light pipes 158) is another wavelength. Thus a plurality of different wavelengths, narrow and/or broadband can be used, depending on the skin problem to be treated.

Figure 15:
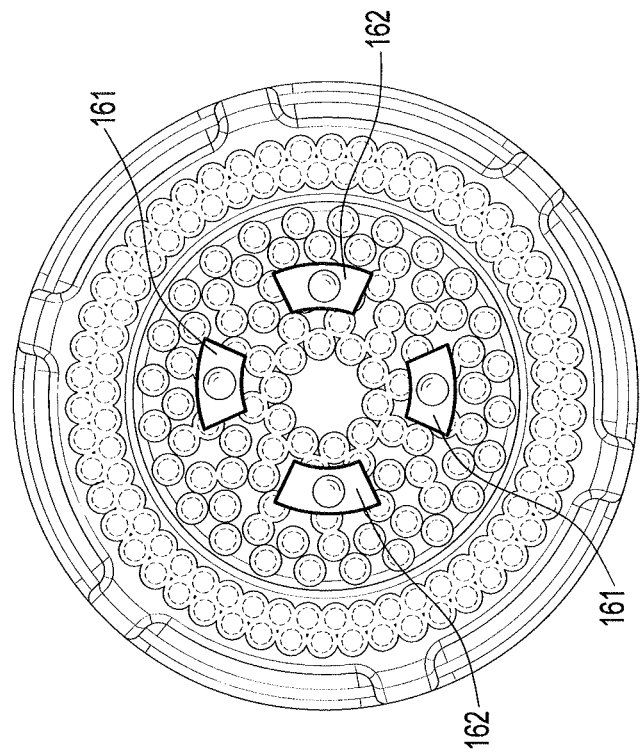
Figure 14:
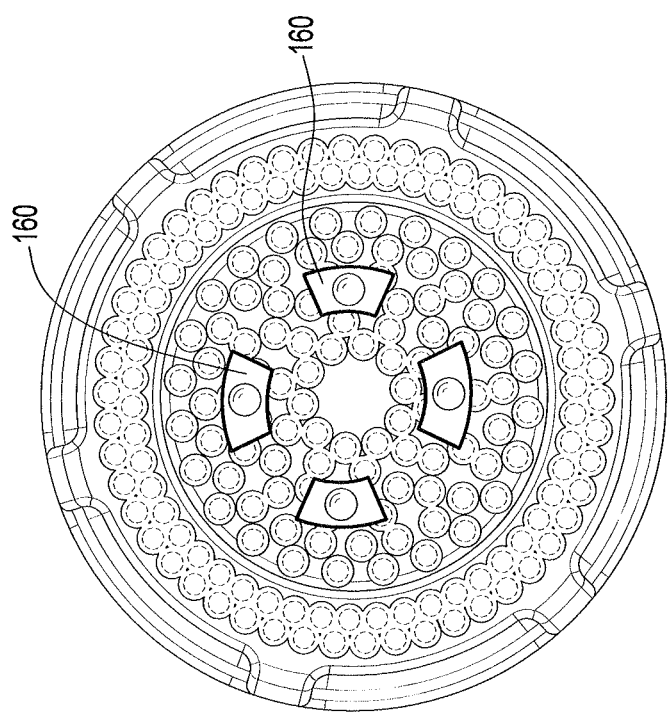
Figure 23:
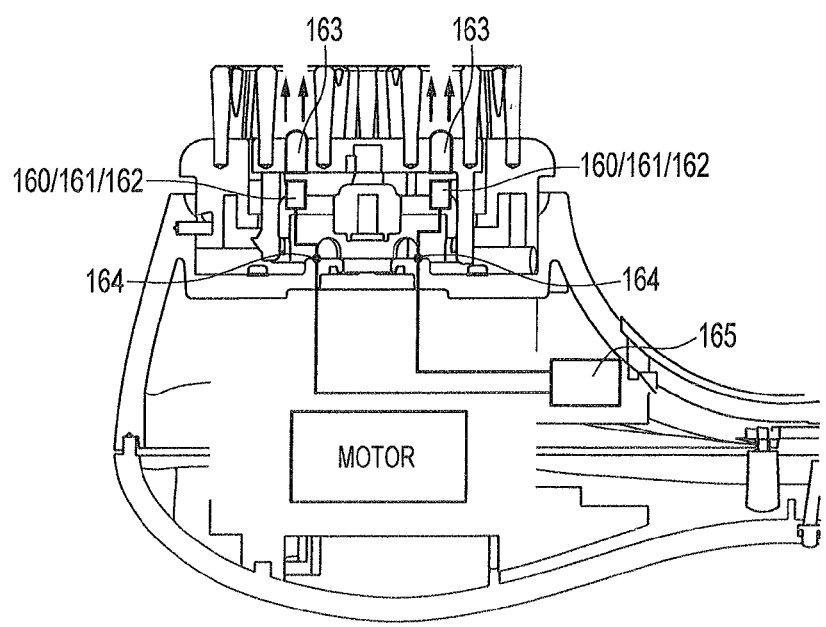

FIGS. 14 and 15 and FIG. 23 show another embodiment, in which light pipes are provided in slots in the inner (oscillating) portion of the brushhead. In FIG. 14, emitters 160 all have one wavelength, while in FIG. 15 emitters 161 have one wavelength and emitters 162 (alternating with emitters 161) have another wavelength. FIG. 23 shows light emitters 160 (FIG. 14) or 161/162 (FIG. 15) in the brushhead, along with light pipes 163 positioned in slots in the brushhead. Electrical connecters 164-164 are provided to the driver circuitry 165 in the handle.

Figure 17:
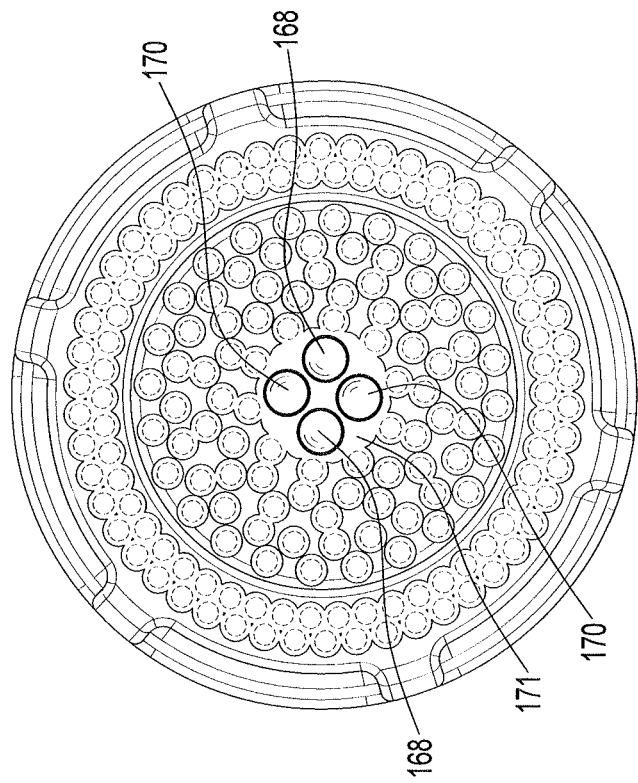
Figure 16:
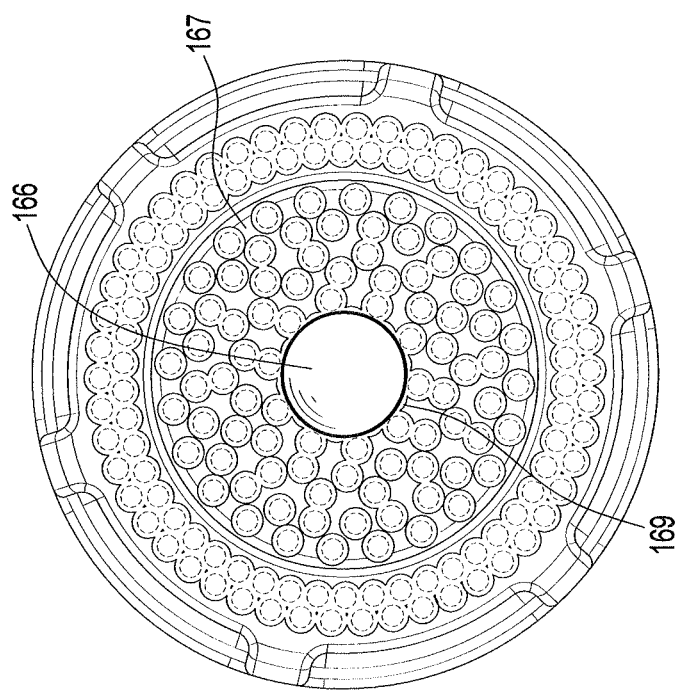
Figure 24:
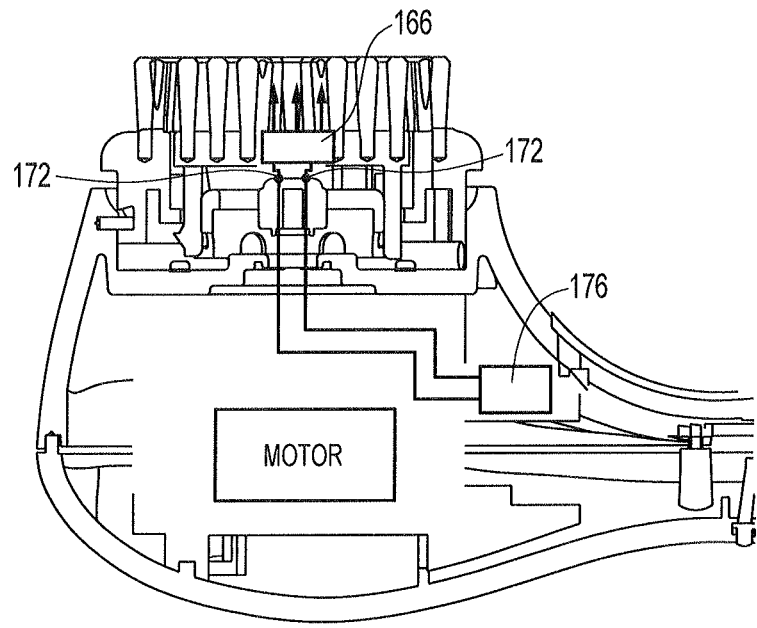

FIGS. 16 and 17 and FIG. 24 show a further embodiment. In FIG. 16, there is a single light emitter 166 in an open center area 169 of the rotating brushhead portion 167, while FIG. 17 shows light emitters 168-168 with one wavelength, and light emitters 170-170 with a second wavelength, all in the center area 171. FIG. 24 shows light emitter 166 within the brushhead with electrical connections 172 at the interface to driver circuitry 176 positioned in the handle.

Figure 19:
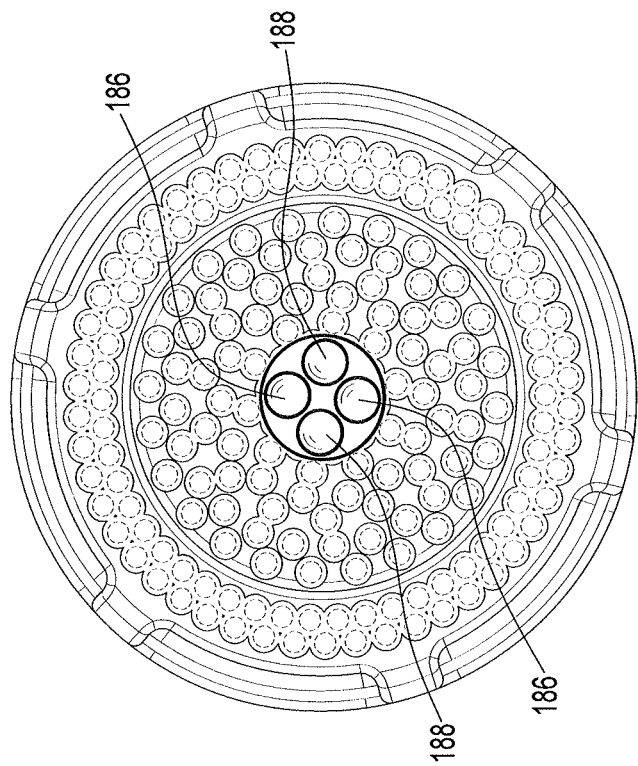
Figure 18:
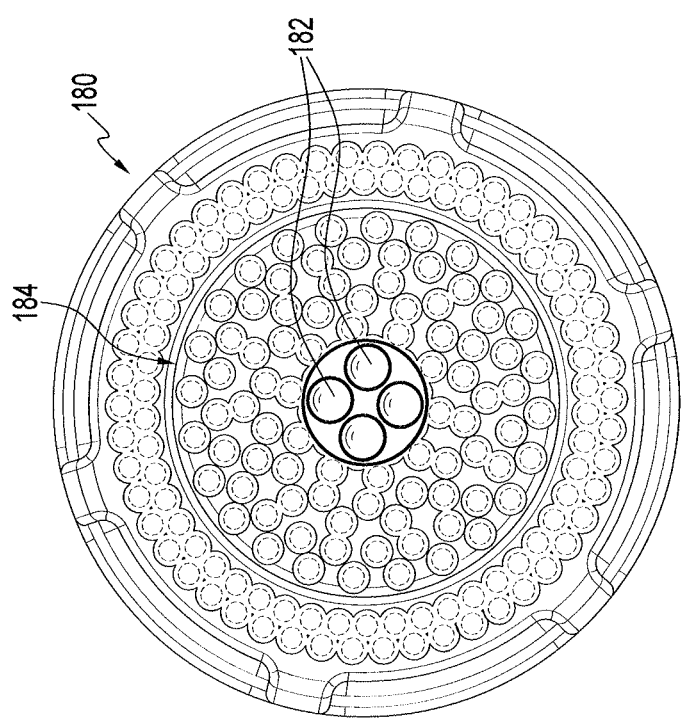
Figure 20:
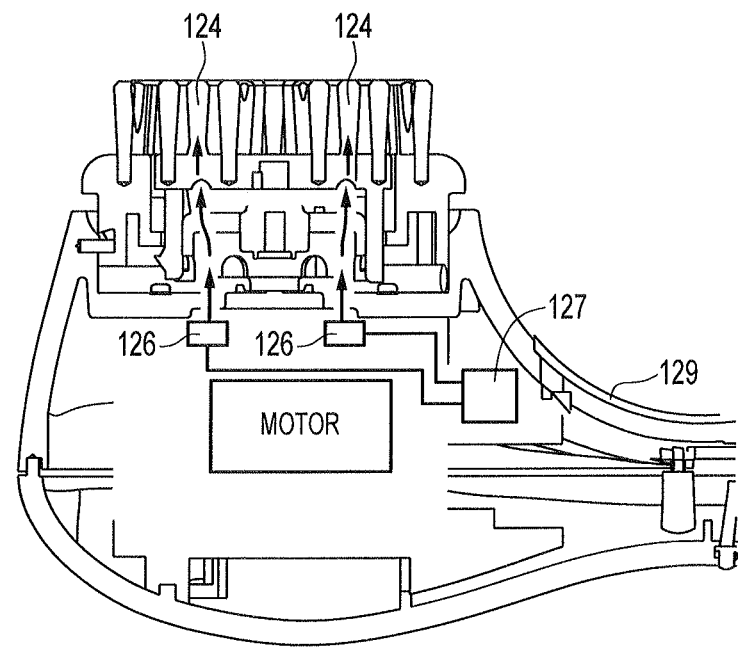
FIGS. 20-25 are side elevational, partially cut-away, views associated with FIGS. 8-19.

FIGS. 18 and 19 show a variation of FIGS. 16 and 17, in which light pipes are provided in slots in the open center area of brushhead 180, transmitting light from light emitters in the handle. FIG. 18 shows a plurality of light pipes 182-182 in the center of oscillating portion 184 of the brushhead, all one wavelength, while FIG. 19 shows light pipes 186-186 producing light with a first wavelength, and light pipes 188-188 having a second wavelength.

Figure 25:
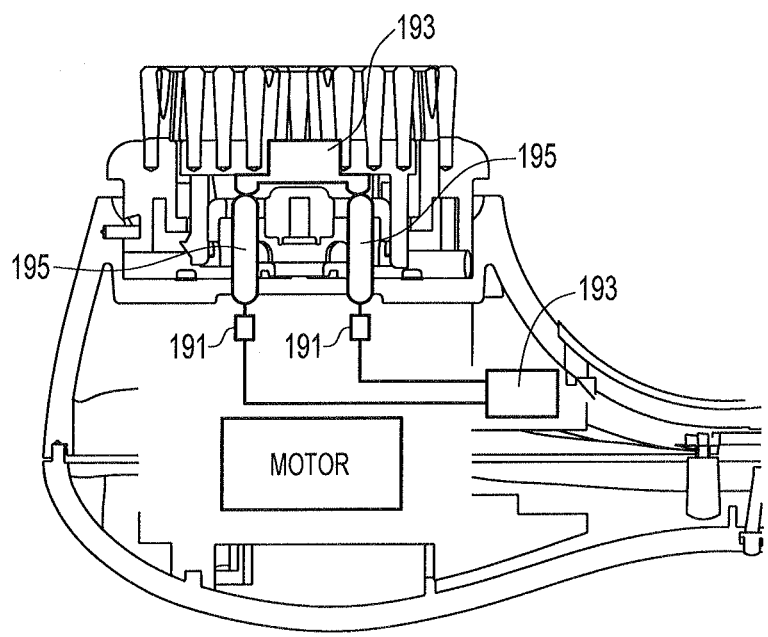

FIG. 25 shows emitters 191-191 located in the handle, along with the driving circuit 193, and bridging light pipes 195 to a light pipe 193 in the center of the brushhead, similar to the single emitter 166 in FIGS. 16 and 24. Multiple light pipes in the center area can also be used, such as shown in FIGS. 18 and 19. The light sources can be either a single wavelength or multiple wavelengths.

In a still further embodiment, the light sources could be mounted or positioned around the periphery of the brushhead, outside of the stationary bristle portion. These light sources could also be a single wavelength or different wavelengths.

In summary, the light sources in the appliance could comprise one or more light emitters positioned in the brush handle or the brushhead itself, with the light being directed through the bristle tufts themselves, or light pipes positioned in slots in the brushhead, or directly from the emitters. The light emitters could have single or multiple wavelengths. The wavelength could be broadband as well.

The light sources in the brushhead (bristle tufts or light pipes or other light transmitting elements) could be located in the outer stationary portion of the brushhead or the inner oscillating portion of the brushhead, or around the periphery of the brushhead, outside of the outer portion.

The combination of the oscillating power brush which flexes the skin by shear stress and exfoliates the skin to a small extent, opening the pores, without damaging the skin, in combination with a plurality of light sources having specific wavelengths associated with treatment of skin conditions, provides a significantly increased efficiency over use of light alone in accomplishing skin treatment. Specifically, the light source/skin brush will enhance the effect of light that targets specific pathogens, such as the porphyrins bacteria for acne, for increased efficacy. Flexing the skin in a rapid fashion permits the light, which is known to propagate only in one direction, to come into contact with more treatment area from different angles within a given period of time than would normally occur with just passing a beam of light over static skin surface.

Other skin conditions may also be treated, with light sources having the appropriate wavelength associated for the particular skin condition. The treatment can be used for a number of different skin conditions, including, for example, skin rejuvenation, collagen treatment, treatment of various infections, treatment of skin, pigmentation, reduction of scar tissue, reduction of inflammation acne, psoriasis, seborrhea, eczema, anti-aging, hair loss, hair renewal, wound treatment, and treatment of certain skin cancers. The above combination can be further combined with the application of topical light-reactive formulations or optical enhancers. The sonic cleansing action of the brush, in the oscillating frequency range of 60-200 Hz, typically resulting in mild exfoliation of the skin, as well as the effect of the light, will produce an enhanced level of absorption and affect the formulations. Certain skin formulations, by improving the optical qualities of the skin, can increase the efficacy of the therapeutic light, by allowing deeper penetration.

It is understood that with light treatments, skin care professionals must remove all physical barriers (e.g. makeup, dead skin cells, etc.) prior to treatment to be effective. The time required for both processes (cleanse and then treat with light) are combined and shortened in the present light-based invention.

The flexing of the skin by the oscillating action of the brush enables light-reactive formulations to be better absorbed, particularly where needed. This increases the effectiveness of reducing the number of pathogenic organisms or cancerous cells, or other therapeutic action, produced by the light itself. The increased absorption is one effect of the brush action; the light sources are then able to activate the formulation-laden pathogens or cells. This allows the formulation and the light to penetrate deeper into the skin for a more effective result, by eliminating the dead skin cells and surface debris. The formulations can be provided either through a source in the appliance, with the aid of a pump or similar action, or separately applied, such as by hand separate from the appliance, followed by the application of brushhead action with the therapeutic light, as described above. The time between the application of the formulation and the use of the therapeutic light skin brush will vary, depending upon the particular formulation.

Figure 26:
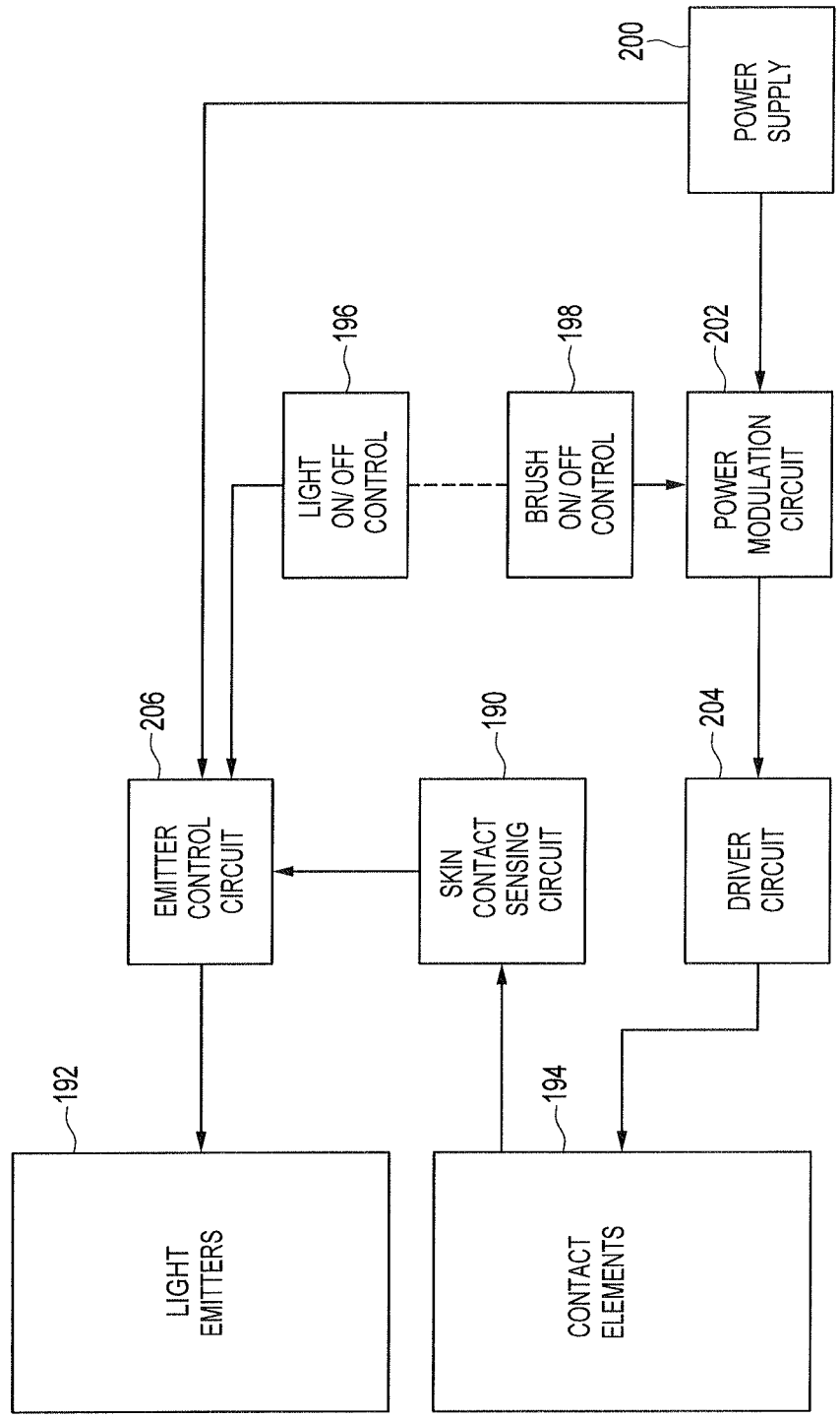
FIG. 26 is a block diagram of the apparatus of FIGS. 8-25, incorporating a sensor control relative to skin contact by the brushhead.

FIG. 26 shows an embodiment which includes a skin contact sensing circuit 190 which activates light emitters 192 in the appliance. The contact elements (the brushhead or other elements) is represented at 194. On/off control switch 196 is for the emitters 192 on/off control switch 198 is for the brushhead. A power supply 200 provides power through a modulation circuit 202 to driver circuit 204 for the brushhead and to an emitter control circuit 206.

In operation, the skin contact sensing circuit 190 will sense when brushhead 194 or other contact element comes into physical contact with the skin. When contact is recognized, sensing circuit 190 will initiate operation of the light emitter control circuit 206, initiating action of light emitters 192. When the sensing circuit 190 recognizes that skin contact has terminated, it will stop emitter 192. This results in longer battery life for the appliance and reduces the possibility of effects on a user's eyes by the emitted light.

Hence, an apparatus has been described which combines a brushhead having an oscillating portion which oscillates through a preferred angle in the range of 5-20° at a frequency in the preferred range of 60-200 Hz to produce a gentle stressing (back and forth, either rotational or other back and forth oscillation) action on the skin, opening the pores and tending to clean and exfoliate slightly the skin, without any damage to the skin. Light sources are provided in the brushhead. The light sources could be LEDs or lasers or other similar light sources. The effect of the light, which has a wavelength or wavelengths associated with treatment of various skin conditions, is enhanced by the action of the brushhead. The light is able to penetrate deeper and provide a more uniform effect. It also has the advantage of increasing the efficacy of formulations particularly adapted for particular skin conditions.

Although a preferred embodiment of the invention has been described for purposes of illustration, it should be understood that various changes, modifications and substitutions are possible within the spirit of the invention, which is defined by the claims which follow.

What is claimed is:

1. An appliance for treatment of skin conditions, comprising:
    a housing member for the appliance;
    a head member having a center of rotation adapted to removably fit to the housing member, wherein the head member in operation rotates back and forth about a rest/neutral position through a selected angle and with a selected frequency;
    a motor assembly for rotating the head member back and forth about the center of rotation; and
    one or more rings of light sources located within the head member, the light sources spaced approximately equally around the circumference thereof or concentric with the circumference thereof, directed at an angle approximately 90° to the circumference thereof, wherein the light sources have driving circuitry associated therewith in the housing member, the light sources having a wave length suitable for treatment of a selected skin condition, thereby permitting light to come into contact with the treatment area of the skin from different angles within a specified period of time, to provide treatment action, wherein the head member and the light sources move together and are removable together from the housing member.

2. The appliance of claim 1, wherein the light is monochromatic.

3. The appliance of claim 1, wherein the light sources all have the same wave length.

4. The appliance of claim 1, wherein the light sources have more than one wave length.

5. The appliance of claim 1, wherein the light is continuous.

6. The appliance of claim 1, wherein the light is pulsed.

7. An appliance for treatment of skin conditions, comprising:
    a housing member for the appliance;
    a head member having a center of rotation adapted to removably fit to the housing member, the head member rotating back and forth about a rest/neutral position through a selected angle and frequency;
    a motor assembly for rotating the head member back and forth about the center of rotation; and
    a plurality of spaced light pipes positioned in openings in the head member, and a plurality of light emitters located within the housing member, the light emitters being apart from the head member, wherein the light from the light emitters is transmitted to the light pipes directly or through an intermediate light pipe positioned in the housing member, wherein the light emitters have driver circuitry associated therewith located in the housing member, wherein the light emitters have a wave length suitable for treatment of a selected skin condition, permitting light to come into contact for the treatment area of the skin from different angles within a specified period of time, to provide treatment action, wherein the head member and the spaced light pipes move together and are removable together from the housing member.

8. The appliance of claim 7, wherein the light is monochromatic.

9. The appliance of claim 7, wherein the light sources all have the same wave length.

10. The appliance of claim 7, wherein the light sources have more than one wave length.

11. The appliance of claim 7, wherein the light is continuous.

12. The appliance of claim 7, wherein the light is pulsed.

* * * * *